United States Patent [19]
Markert et al.

[11] Patent Number: 4,881,402
[45] Date of Patent: Nov. 21, 1989

[54] PROCESS FOR THE DETERMINATION OF LIQUID ABSORPTION OF POWDERY SOLIDS

[75] Inventors: Jurgen Markert, Dulmen; Klaus-Dieter Schubel, Datteln; Milan Krizek, Marl, all of Fed. Rep. of Germany

[73] Assignee: Huels Aktiengesellschaft, Marl, Fed. Rep. of Germany

[21] Appl. No.: 233,743

[22] Filed: Aug. 19, 1988

[30] Foreign Application Priority Data

Aug. 20, 1987 [DE] Fed. Rep. of Germany ....... 3727794

[51] Int. Cl.[4] ............................................. G01N 13/00
[52] U.S. Cl. ...................................... 73/61 R; 73/73; 73/53
[58] Field of Search ................ 73/61.1 R, 53, 73, 866, 73/865.3, 74

[56] References Cited

U.S. PATENT DOCUMENTS

| | | | |
|---|---|---|---|
| 3,952,584 | 4/1976 | Lichstein | 73/73 |
| 4,003,981 | 1/1977 | Turk et al. | 423/335 |
| 4,062,228 | 12/1977 | Peak | 73/74 |
| 4,560,524 | 12/1985 | Smuckler | 264/105 |

FOREIGN PATENT DOCUMENTS 3606356 9/1987 Fed. Rep. of Germany .

OTHER PUBLICATIONS

ATSM D 2414-82.

Primary Examiner—Hezron E. Williams
Attorney, Agent, or Firm—Oblon, Spivak, McClelland, Maier & Neustadt

[57] ABSTRACT

A process for measuring the liquid absorption capacity of a powder includes the step of spraying a liquid in the form of a spray cone at a constant throughput from at least one spraying device onto a powder being stirred in the mixing chamber of a mixer, the powder filling between 10 to 80% of the mixing chamber. The torque of the stirrer of the mixer is measured both before and during the spraying step, and from this measurement both a maximum level of the torque and the time difference between the beginning of the spraying step and the time when the maximum level is reached are determined. An amount of liquid absorption of the powder is then determined based upon the liquid mass which is sprayed during that time difference.

4 Claims, 1 Drawing Sheet

PROCESS FOR THE DETERMINATION OF LIQUID ABSORPTION OF POWDERY SOLIDS

BACKGROUND OF THE INVENTION

The invention relates to a process for measurement of the liquid absorption of powdery solids. The invention aims at reproducibly determining the maximum possible amount of liquid that powdery solids can absorb up to saturation.

Powdery solids, such as, for example, mineral fillers for rubber processing, carbon blacks and pigments, have the property of being able to absorb liquids without losing their powder form. The amount of liquid that the powdery solids can absorb at most, i.e., until saturation occurs, is especially important. A powdery solid—hereinafter called powder—is a mineral filler, a pigment or a carbon black, whose bulk density can vary in a broad range, down to extremely low values of the bulk density.

The liquid absorption—hereafter abbreviated LA—is used to determine the surface properties of the powder and gives indications of the powder structure and the processing properties of the powder. Examples of this are the "DBP number" (Dibutylphthalate number) in carbon blacks and light-colored fillers as well as the "oil number" in pigments and fillers.

According to DIN 53 601 (Dec. 78) and ASTM D 2414-82 dibutylphthalate (DBP) absorption of carbon blacks is determined with the Cabot absorptometer. For this purpose, the amount of DBP is measured which was dripped at room temperature onto the carbon black stirred in the maximum absorptometer until reaching a preset torque, which is clearly below the torque. The empty volume of the carbon black can be estimated and indications of its processing properties can be derived from the DBP absorption. In DIN 53 601 the oil feeding is automatically cut off at a torque of about 70% of the maximum occurring torque. Further, two calibrating carbon blacks are used in this process.

The kneading chamber of the Cabot Absorptomer has a volume of about 50 cm$^3$, the rotor pair runs with a rotation ratio of 125 to 250 per minute.

Generally 20 g at a bulk density of 0.5 g/cm$^3$ is recommended as carbon black amount. The degree of fullness then is 80%. In any case, the kneading chamber must be adequately filled, since false measurements result in insufficiently filled kneading chambers. The DBP runs with constant speed of 4 ml per minute (but pulsing) on the stirred carbon black.

It is further known, according to the oil number according to DIN ISO 787 (Feb. 1983) to determine the amount of refined linseed oil, which is absorbed by a pigment or filler sample under established conditions. In this case a sample amount of pigment or filler is put on a glass plate and some drops of refined linseed oil are dropped on it at room temperature. The oil is rubbed into the sample amount with a knife spatula. Dropping of oil and rubbing it into the sample amount are repeated several times, until a soft paste results, i.e., until the powder has lost its powder form. Recognition of the end point of the oil addition depends on the tester. The oil numbers determined according to this process therefore are preferably considered as relative values of a testing position (between sample and comparison sample).

In both methods the liquid (DBP or refined linseed oil) is added to the stirred or rubbed powder at room temperature, as pulsing sharp jet in the Cabot Absorptometer or as drops in the oil number method. Thus, the powder particles are locally overloaded with liquid, as a result of which the measurement results are adversely affected.

SUMMARY OF THE INVENTION

The object of the invention is to find a process for measuring the LA of powders, which is applicable to a broad range of bulk densities from extremely low to high values, and the powder is swirled during application of the liquid.

This and other objects are achieved according to the present invention by a process for measuring the liquid absorption capacity of a powder, the process comprising the steps of stirring the powder in a mixing chamber of a planetary mixer, the mixing chamber being between 10 and 80% filled with the powder, spraying a liquid in the form of a spray cone and at a throughput which is constant over time, onto the powder from at least one spraying device, the liquid being heated to have a viscosity of 0.1 to 50 mPa·s at shear rates of $5 \times 10^3$/sec. to $5 \times 10^6$/sec., the constant throughput having such a value that a liquid mass of 0.05 to 6 times the mass of the powder is sprayed in 0.1 to 10 minutes. The torque of a stirrer of the mixer is measured before and during the spraying step and both a maximum level of the torque and a time difference between the beginning of the spraying step and a time when the maximum level is reached are determined. An amount of liquid absorption of the powder is then determined, based on the liquid mass which is sprayed during the time difference.

By low-force stirring the shear, tensile and compressive forces acting on the powder particles are kept small, since the chamber volume is filled only to 10 to 80% (preferably 10 to 40%) with powder. The revolutions per minute and the peripheral speeds are approximately in the following ranges:

revolutions per minute of the drive: 40 to 100 per minute peripheral speed of the stirrer or of the scraper (planetary movement): 3600 to 9300 cm per minute peripheral speed of the stirrer (autorotation): 5900 to 14900 cm per minute.

All gaps between the impellers and the wall of the mixing chamber are at least twenty times as great as the average diameter of the powder particles.

The liquid is fed pulse-free to the applicator from a storage tank and (preferably above the stirred powder) is finely sprayed in the form of a (hollow or solid) spray cone and delivered down on the powder. For this purpose, one or more spray devices are used, which can be operated as one-material or two-material nozzle with moderately great pressure or with high pressure.

The liquid throughput through the applicator is adjusted to a valve that is constant over time. For 0.1 to 10 minutes a mass of liquid is sprayed on, which corresponds to 0.05–6 times the mass of the powder which is in the mixing chamber. The viscosity of the liquid, if needed, is adjusted by preheating to 0.1 to 50 mPa·s at shear rates of $5 \times 10^3$ to $5 \times 10^6$ per second at the narrowest point of the spray nozzle. Optionally, the suitable viscosity is reached at increased temperature depending on the nature of the liquid to be applied.

The mixer drive is equipped with a known device for measuring the torque. The course of the torque over time is preferably registered on a recorder. The fluctuations of the register curve possibly occurring, which originate from secondary influences, are not further considered or are eliminated in the evaluation by the process of the moving average.

With increasing amount of the sprayed-on liquid the torque increase rises slowly at first and later steeply to a maximum; in some cases, more than one point of inflection can be observed in the rising area of the curve. After reaching the maximum, the torque generally decreases rapidly. The amount of liquid sprayed on the powder up to the maximum of the torque, the time difference from the beginning of the spraying to the maximum ($t_{max}-t_0$) as well as the level of the maximum ($M_{max}-M_0$) are measured.

The process of the invention has the following properties and advantages:

- The LA can also be measured for powders with extremely low bulk density, in which up to now no reproducible measurements were possible.
- It is applicable for powder with extremely low, medium and high bulk density—in other words from 0.02 to 3 g/cm$^3$, preferably 0.04 to 1.2 g/cm$^3$—and thus is universally applicable.
- Local overloading of the powder particles with liquid and thus a falsification of the measuring results are avoided by the uniform distribution of the sprayed-on liquid.
- Liquids of entirely different nature can be applied, since their viscosity up to a suitable value for the formation of a spray mist is adjusted by increasing the liquid temperature.
- The powder particles are only slightly stressed; their surfaces are very easily accessible for the sprayed-on liquid.
- By the extensive separation of the powder particles the apparent structures usually caused by agglomerate formation with narrow interstices between the particles are avoided. Thus, basically only the LA on and within the powder particles themselves is determined.
- "Calibrating powders," such as, e.g., calibrating carbon blacks are not used.
- The LA is measured until reaching the maximum torque (and somewhat more).
- The chamber volume can be filled with powder up to 80%, the mass of the applied liquid can be up to six times the mass of the powder and the spraying time can be up to 10 minutes.

DETAILED DESCRIPTION OF THE PREFERRED EMBODIMENTS

Figure 1:
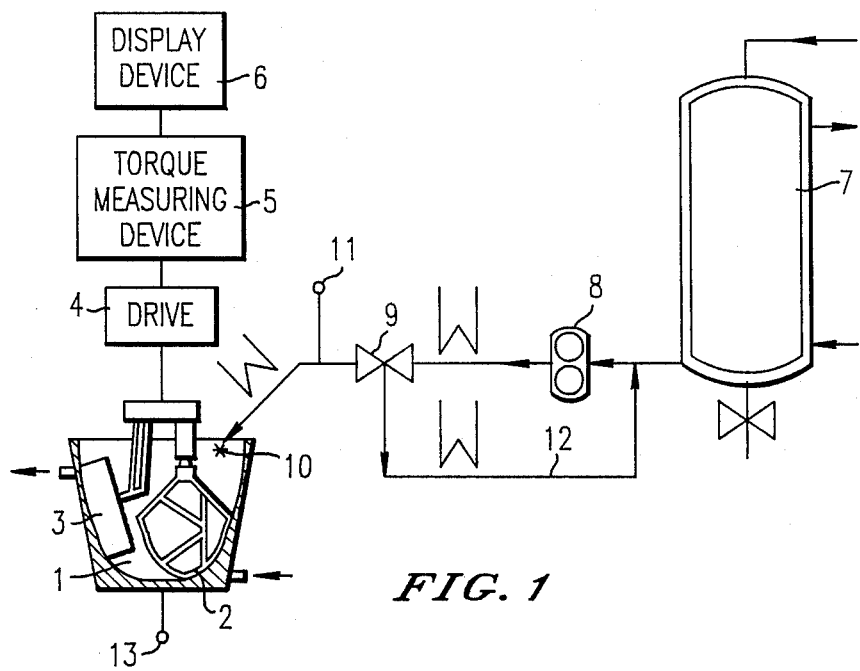
FIG. 1 is a schematic view of the device used for carrying out the method of the invention.

FIG. 1 shows, by way of example, a device for carrying out the process of the invention. Mixing vessel (1) (with liquid jacket for constant temperature control) contains a planetary stirrer consisting of rotating stirring blades (2) and scraper (3), which is driven by drive (4) (with adjustable speed and speed regulation). The stirrer drive is connected to torque measuring device (5) (with several torque measuring ranges) and the latter is connected to display device (6).

Storage tank (7) (if necessary, with liquid jacket for constant temperature control for the liquid to be applied is connected by a pipe to a gear pump (8) (with excess-pressure safety device), which on the pressure side is connected by a three-way valve (9) to spray device (10), which is fastened in the cover of the mixing vessel. Pressure measuring point (11) is ahead of the spray nozzle. Valve (9), moreover, is connected, by return pipe (12), to the suction side of the gear pump. The temperature of the swirled powder, if necessary, is measured with temperature sensor (13). All pipes between the storage tank and spray nozzle as well as the return pipe can be heated, preferably electrically. The gear pump and the valve are thermally insulated.

All secondary devices for carrying out the process of the invention are not shown in FIG. 1.

The process of the invention is performed by means of the device represented in FIG. 1, for example, as follows: the heatable storage tank is filled with the liquid to be applied and—if necessary—brought to the preset temperature, so that the viscosity of the liquid is in the indicated range. If necessary, the heating of the pipes is adjusted to the same temperature. The three-way valve is opened to the return pipe and closed to the pipe of the spray device; the gear pump is turned on and adjusted to a throughput, which is greater than the liquid stream necessary for the spraying.

The mixing vessel, which is at room temperature or—if necessary—thermostated, is charged with powder that is at room temperature. The still liquid-free powder is swirled until a constant torque is established; this is generally reached after about 0.1 to 1 minute. Then the three-way valve is reversed, and the pressure necessary for the spraying and the preset liquid stream—determined in a preliminary test—is established ahead of the spraying nozzle within a few seconds. During spraying of the liquid the torque is again recorded until the maximum of the torque curve is reliably discernible.

The process can largely be automated according to known methods.

The time that has passed from the beginning of the liquid application to reaching the torque maximum is gathered from the torque curve. The absolute LA is the product of the volume throughout of the liquid and the duration of the liquid application to the maximum torque; the volume throughput can be converted into the mass throughput by means of the density of the liquid. The relative LA is obtained if the absolute LA is divided by the mass of the powder present in the mixing vessel.

The process of the invention is further explained by the following example for which a device corresponding to FIG. 1 is used.

The storage tank is filled with ethylene glycol. 100 g (corresponding to 833 $cm^3$ of density volume) of powdery active silicic acid is fed in the mixing vessel at room temperature with 2.5-liter chamber volume. The still liquid-free powder is first stirred and swirled for about 1 minute at a speed of the drive of 75 rpm. During this time a constant torque is established on the stirrer. The ethylene glycol circulates by gear pump and return pipe at room temperature. The speed of the gear pump is established in a preliminary test at the pressure of 6 bars desired for the spray nozzle. After expiration of one minute the three-way valve is reversed. Within a few seconds a constant pressure of 6 bars is built up ahead of the spray nozzle. The liquid is delivered with 72 millimeter per minute, sprayed through the nozzle (hollow cone spraying), sprayed on the stirred powder and absorbed by it.

During the test (including the lead time) the torque is registered as a function of time. The test is ended when the maximum of the torque curve is exceeded and is clearly recognizable and can be reliably determined.

In the present test the maximum of the torque curve is reached after 298 seconds, calculated from the beginning of the spraying-on of the ethylene glycol; the test is stopped after about 340 seconds. Until the maximum of the torque the active silicic acid absorbed 357.6 milliliters of ethylene glycol. The torque at the maximum is about 6 newton-meters.

Analogously to this example different carbon blacks and light-colored fillers are tested, in which the LA cannot be measured with the thus far usual methods.

Figure 2:
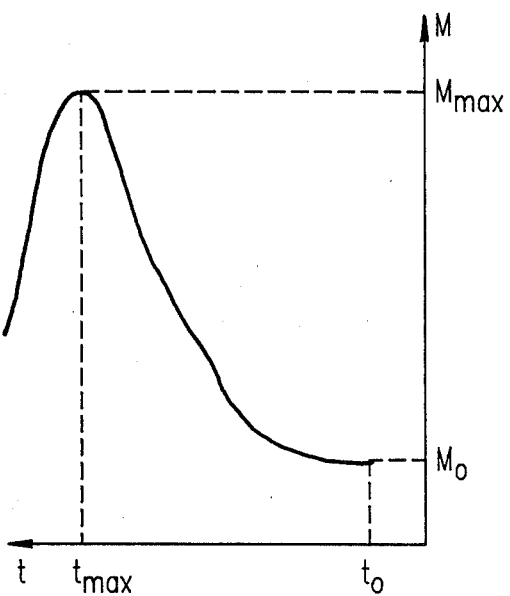
FIG. 2 is a graph showing a torque curve for a mixer.

A typical curve for the process of the invention is represented in FIG. 2. Torque M is plotted as a function of time t. Up to moment $t_o$ of the beginning of the liquid application constant torque $M_o$ has been established. At moment $t_{max}$ the maximum of torque $M_{max}$ is reached. Time $t_{max}$ belonging to the maximum can be gathered directly from the curve. The LA of the powder is calculated by the difference $t_{max}-t_o$.

Difference $t_{max}-t_o$ according to experience is between 0.1 and 8 minutes.

We claim:

1. A process for measuring the liquid absorption capacity of a powder, comprising the steps of:

stirring the powder in a mixing chamber of a planetary mixer, the mixing chamber being between 10% and 80% filled with the powder;

spraying a liquid in the form of a spray cone, and at a throughput which is constant over time, onto the powder from at least one spraying device, said liquid being heated to have a viscosity of 0.1 to 50 mPa·s at shear rates of $5\times10^3$/sec. to $5\times10^6$/sec., said constant throughput having such a value that a liquid mass of 0.05 to 6 times the mass of the powder is sprayed in 0.1 to 10 minutes;

measuring a torque of a stirrer of said mixer before and during said spraying step;

determining a maximum level of said torque and a time difference between the beginning of said spraying step and a time when said maximum level is reached; and determining an amount of liquid absorption of the powder based on the liquid mass which is sprayed during said time difference.

2. The process of claim 1 wherein the mixing chamber is between 10% and 40% filled with the powder.

3. The process of claim 1 wherein the powder has a bulk density of 0.02 to 3 g/cm$^3$.

4. The process of claim 1 wherein the powder has a bulk density of 0.4 to 1.2 g/cm$^3$.

* * * * *